(12) United States Patent
Coleman et al.

(10) Patent No.: US 8,016,883 B2
(45) Date of Patent: Sep. 13, 2011

(54) METHODS AND DEVICES FOR ROTATOR CUFF REPAIR

(75) Inventors: Struan Coleman, New York, NY (US); David P. Martin, Arlington, MA (US); Said Rizk, Salem, NH (US); Ajay Ahuja, Needham, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 690 days.

(21) Appl. No.: 11/671,102

(22) Filed: Feb. 5, 2007

(65) Prior Publication Data

US 2007/0198087 A1 Aug. 23, 2007

Related U.S. Application Data

(60) Provisional application No. 60/765,840, filed on Feb. 7, 2006.

(51) Int. Cl.
*A61F 2/08* (2006.01)

(52) U.S. Cl. .................................. 623/13.11

(58) Field of Classification Search ............... 623/13.11, 623/13.17, 13.18, 23.72, 23.75, 926
See application file for complete search history.

(56) References Cited

U.S. PATENT DOCUMENTS

| | | | |
|---|---|---|---|
| 5,527,341 | A | 6/1996 | Gogolewski et al. |
| 5,811,272 | A | 9/1998 | Snell et al. |
| 6,245,537 | B1 | 6/2001 | Williams et al. |
| 6,316,262 | B1 | 11/2001 | Huisman et al. |
| 6,323,010 | B1 | 11/2001 | Skraly et al. |
| 6,514,515 | B1 | 2/2003 | Williams |
| 6,548,569 | B1 | 4/2003 | Williams et al. |
| 6,867,247 | B2 | 3/2005 | Williams et al. |
| 2003/0211131 | A1 | 11/2003 | Martin et al. |
| 2004/0234576 | A1 | 11/2004 | Martin et al. |

FOREIGN PATENT DOCUMENTS

| | | |
|---|---|---|
| WO | WO 99/32536 | 7/1999 |
| WO | WO 00/51662 | 9/2000 |
| WO | WO 00/56376 | 9/2000 |
| WO | WO 01/32229 | 5/2001 |

OTHER PUBLICATIONS

Ito and Morioka, "Surgical treatment for large and massive tears of the rotator cuff", *Int. Orthop.*, 27(4):228-31 (2003).
Mura, et al., "Biomechanical effect of patch graft for large rotator cuff tears: a cadaver study", *Clin. Orthop. Relat. Res.*, (415):131-8 (2003).
Galatz, et. al., "The outcome and repair integrity of completely arthroscopically repaired large and massive rotator cuff tears", *J. Bone Joint Surg. Am.*, 86-A(2):219-24 (2004).
Williams, et al. Applications of PHAs in Medicine and Pharmacy, in Biopolymers, *Polyesters, III* vol. 4:91-127 (2002).
Steinbüchel, "Polyhydroxyalkanoic acids", *Biomaterials*, 123-213 (1991).
Steinbüchel, et al., "Diversity of Bacterial Polyhydroxyalkanoic Acids", *FEMS Microbial. Lett.*, 128:219-228 (1995).
"Tepha Announces Submission of Devce Master File to FDA" retrieved from http://www.pressreleases.be/script_UK/newsdetail.asp?ndays+m$ID=695 on Dec. 17, 2004.

*Primary Examiner* — Suzette J Gherbi
(74) *Attorney, Agent, or Firm* — Pabst Patent Group LLP

(57) ABSTRACT

Interposition and augmentation devices for tendon and ligament repair, including rotator cuff repair, have been developed as well as methods for their delivery using arthroscopic methods. The devices are preferably derived from biocompatible polyhydroxyalkanoates, and preferably from copolymers or homopolymers of 4-hydroxybutyrate. The devices may be delivered arthroscopically, and offer additional benefits such as support for the surgical repair, high initial strength, prolonged strength retention in vivo, flexibility, anti-adhesion properties, improved biocompatibility, an ability to remodel in vivo to healthy tissue, minimal risk for disease transmission or to potentiate infection, options for fixation including sufficiently high strength to prevent suture pull out or other detachment of the implanted device, eventual absorption eliminating future risk of foreign body reactions or interference with subsequent procedures, competitive cost, and long-term mechanical stability. The devices are also particularly suitable for use in pediatric populations where their eventual absorption should not hinder growth.

22 Claims, No Drawings

US 8,016,883 B2

METHODS AND DEVICES FOR ROTATOR CUFF REPAIR

CROSS-REFERENCE TO RELATED APPLICATIONS

The application claims priority to U.S. Ser. No. 60/765,840, filed Feb. 7, 2006.

The United States government has certain rights in this invention by virtue of Grant Number IR43 AR052557-01-AI "Arthroscopic rotator cuff repair device" National Institute of Arthritis and Musculosketal and Skin Diseases.

FIELD OF THE INVENTION

The present invention generally relates to methods for repairing rotator cuff tendons using devices comprising polyhydroxyalkanoate polymers.

BACKGROUND OF THE INVENTION

The rotator cuff is a confluence of tendons that connect the muscles originating around the scapula and inserting on the upper humerus. When activated, these muscles raise, lower, and rotate the arm. The rotator cuff tendons measure about 5 cm in width, on average, and together they form a cuff that encapsulates the article surface at the top of the humerus. The acromion (the bone on the top of the shoulder) forms a bony and ligamentous arch over the rotator cuff and is bordered by the acromioclavicular ligament, the coracoid (the bone in front of the shoulder), and the acromioclavicular joint.

The rotator cuff can be inured by a number of different mechanisms. For example, if a person falls and lands on his shoulder, the acromion can strike the rotator cuff causing injury to the muscles or tendons. The extent of the injury, which can be either a bruise or tear, depends on the position of the arm during the fall, the strength and flexibility of the muscles and tendons, and the geometry of the undersurface of the acromion.

When the cuff is bruised, bleeding into the tendons may occur, and the tendons can swell, causing the cuff to be compressed, given the relative narrowness of the space provided for the cuff. This condition may persist for some months and is typically characterized by weakness and pain, especially when the outstretched arm is raised to the side or rotated. Symptoms are usually self-limited after appropriate treatment.

A torn rotator cuff is a significantly more serious problem. Symptoms are similar, although nighttime pain is often more intense, and the ability of the muscle to move the arm is significantly weakened, resulting in limited motion. If the condition does not stabilize over time with rest and supportive care, surgery is often recommended (especially in cases where the cuff tear is significant, and/or in order to prevent the development of osteoarthritis). The size of the tear is typically determined using an arthrogram or by MRI.

While the surgical repair has historically been performed as an open procedure (and more recently as a "mini-open" repair), the majority of rotator cuff repairs are now repaired fully arthroscopically, with the tendon being reattached directly to the bony insertion on the lateral borer of the humerus. However, when direct reattachment is not possible, for example, because retraction of the muscle has created a large defect, interposition devices or grafts (including synthetic cuff prostheses) are used to fill the defect. Devices (or grafts) are also used as augmentation devices to strengthen a repair to prevent recurrent tears and allow for a more aggressive rehabilitation particularly in younger patients.

Autologous grafts, including tendon, muscle and fascia lata are all used in rotator cuff repair (Ito, J. and Morioka, T. *Int. Orthop.* 27:228-231, 2003). Biologic and synthetic prosthetic grafts, which avoid the morbidity associated with the use of an autograft, are also used to repair rotator cuff injuries and include, for example: freeze-dried rotator cuff allografts, PTEF felt (marketed by Davol Inc.), carbon filament (Mura, N. et al. *Clin. Orthop.* 415:131-138, 2003); and more recently, the RESTORE® Orthobiologic Soft Tissue Implant manufactured from small intestine submucosa (marked by DePuy), the GraftJacket™ manufactured from decellularized dermis (marketed by Wright Medical), the TissueMend® manufactured from collagen (marketed by Stryker Orthopedics), and the Zimmer® Collagen Repair Patch manufactured from chemically crosslinked, acellular collagen.

Notably, despite the fact that the majority of repairs are now performed arthroscopically, and that recent reports indicate a high percentage of recurrent defects after arthroscopic repair of large and massive rotator cuff tears in particular, there is currently no interposition or augmentation device that has been designed specifically for arthroscopic rotator cuff repair (Galatz, I., M. et. al., *J. Bone Joint Surg. Am.* 86-A: 219-224, 2004).

It is estimates that approximately 250,000 rotator cuff repair procedures are performed each year to alleviate the persistent pain and discomfort associated with shoulder injuries, and help patients regain full range of motion. There is thus a significant need to develop interposition and augmentation devices to fill a defect or augment a repair that can reduce the percentage of recurrent defects. There is also a need to develop interposition and augmentation devices that can be delivered arthroscipiclly.

It is therefore an object of this invention to provide new medical devices for rotator cuff repair that can be used as interposition or augmentation devices wherein the devices have one or more of the following features; high initial strength, prolonged strength retention in vivo, sufficient mechanical properties to provide support for the surgical repair, flexibility, anti-adhesion properties, favorable tissue response upon implantation, degradation in vivo to a natural metabolite, minimal risk for disease transmission or to potentiate infection, capacity to remodel in vivo into healthy tissue, and/or sufficient material strength to prevent suture pull out or failure if other fixation is used.

In is another object of this invention to provide methods for fabricating interposition and augmentation devices for rotator cuff repair as well as other tendon and ligament repairs.

It is yet another object of this invention to provide methods for delivering the interposition and augmentation devices for rotator cuff repair, and generally for other tendon/ligament repairs, specifically including arthroscopic methods of delivery.

SUMMARY OF THE INVENTION

Interposition and augmentation devices for rotator cuff repair have been developed as well as methods for their delivery using arthroscopic methods. The devices are preferably derived from biocompatible polyhydroxyalkanoates, and preferably from copolymers or homopolymers of 4-hydroxybutyrate. The devices may be delivered arthroscopically, and offer additional benefits such as support for the surgical repair, high initial strength, prolonged strength retention in vivo, flexibility, anti-adhesion properties, improved biocompatibility, an ability to remodel in vivo to healthy tissue, minimal risk for disease transmission or to potentiate infection, options for fixation including sufficiently high strength to prevent suture pull out or other detachment of the implanted device, eventual absorption eliminating future risk of foreign body reactions or interference with subsequent procedures, competitive cost, and long-term mechanical stability. The device are particularly suitable for use in pediatric populations where their eventual absorption should not hinder growth. PHA interposition or augmentation devices for rotator cuff repair should be useful in the treatment of patients with torn rotator cuffs, and are expected to decrease the high percentage of recurrent defects.

DETAILED DESCRIPTION OF THE INVENTION

Interposition and augmentation devices for rotator cuff repair have been developed. These devices can be manufactured to allow their use and application in arthroscopic rotator cuff repair procedures.

I. Definitions

"Biocompatible" as used herein means the biological response to the material or device is appropriate for the device's intended application in vivo. Any metabolizes of these materials should be biocompatible.

"Strength retention" as used herein refers to the amount of strength that a material maintains over a period of time following implantation into a human or animal. For example, if the tensile strength of an absorbable mesh or fiber decreases by half over three months when implanted into an animal or human, the mesh or fiber's strength retention at 3 months would be 50%.

"Polydroxyalkanoate" as used herein, refers to any polymer comprising a polyester structure that can be produced by a wildtype or transgenic organism. It may also be referred to as a PHA.

"Poly-4-hydroxybutyrate" as used herein refers to a homopolymer comprising 4-hydroxybutyrate units. It may be refereed to as TephaFLEX™, P4HB or PHA4400.

"Copolymers of poly-4-hydroxybutyrate" as used herein refers to any polymers comprising 4-hydroxybutyrate with one or more different hydroxy acid units.

"Absorbable" as used herein means the complete degradation of a material in vivo, and elimination of its metabolites from an animal or human.

"Augmentation device (or graft)" as used herein refers to a material that can be used to strengthen a rotator cuff repair. For example, a surgeon may enhance the strength of a rotator cuff repair made with sutures by incorporating a reinforcing material into the repair.

"Interposition device (or graft)" as used herein refers to a material that is used to bridge a gap (or defect) between the end of a tendon and its bony insertion site.

II. Polymers

Poly-4-hydroxybutyrate is a strong, pliable thermoplastic that is produced by a fermentation process (see U.S. Pat. No. 6,548,569 to Williams et al.). The polymer belongs to a larger class of materials called polyhydroxyalkanoates (PHAs) that are produced by numerous microorganisms, Steinbüchel. A. Polyhydroxyalkanoic acids, *Biomaterials*, 123-213 (1991); and Steinbüchel A., et al. Diversity of Bacterial Polyhydroxyalkanoic Acids, *FEMS Microbial. Lett.* 128:219-228 (1995). In nature these polyesters are produced as storage granules inside cells, and serve to regulate energy metabolism. They are also of commercial interest because of their thermoplastic properties, and relative ease of production.

Tepha, Inc. (Cambridge, Mass.) produces poly-4-hydroxybutyrate under the TephaFLEX® tradename, and related copolymers for medical use, and it has filed a Device Master File with the United States Food and Drug Administration (FDA) for the TephaFLEX polymer. Related copolymers include 4-hydroxybutyrate copolymerized with 3-hydroxybutyrate (produced by Tepha, Inc. under the TephELAST® tradename) or glycolic acid (U.S. patent application publication number US 2003/0211131 to Martin & Skraly, U.S. Pat. No. 6,316,262 to Huisman et al., and U.S. Pat. No. 6,323,010 to Skraly et al.). Tepha has also filed a Device Master File with the United States FDA for its TephELAST® copolymers which contain 3-hydroxybutyrate and 4-hydroxybutyrate. Methods to control molecular weight of PHA polymers are disclosed by U.S. Pat. No. 5,811,272 to Snell et al., and methods to purify PHA polymers for medical use are disclosed by U.S. Pat. No. 6,245,537 to Williams et al. PHAs with degradation rates in vivo of less than one year are disclosed by U.S. Pat. No. 6,548,569 to Williams et al. and PCT WO 99/32536 to Martin et al. The use of PHAs as tissue engineering scaffolds are disclosed by U.S. Pat. No. 6,514,515 to Williams, and other applications of PHAs have been reviewed in Williams, S. F., et al. Applications of PHAs in Medicine and Pharmacy, in Biopolymers, *Polyesters, III* Vol. 4:91-127 (2002). U.S. Pat. No. 6,867,247 Williams et al. dislcoses rivets and tacks made from PHAs for use in rotator cuff repair.

III. Devices

Augmentation and Interposition Devices

Augmentation and interposition devices comprising PHAs, and more specifically poly-4-hydroxybutyrate and copolymers thereof, which are absorbable, and to methods for making and delivering such devices for the repair of rotator cuff terms and other tendon or ligament repairs, have been developed. The devices comprise PHA fibers that provide high initial strength and prolonged strength retention when implanted in vivo, and may incorporate other PHA components, such as PHA non-woven textiles, or other materials that are biocompatible. These devices should be at least partly porous, ideally with pore sizes of at least 10 microns, and be suitable to encourage tissue in-growth.

The deceives should degrade over time following implantation, and improve the long-term outcome of rotator cuff repair. Preferably the devices degrade to non-inflammatory metabolites that are already present in the body. The devices may be replaced by new tissue as they are remodeled in vivo. During the early stages of the remodeling process it is desirable for the devices to retain sufficient strength to provide an effective repair. Ideally, the devices should permit a patient to undergo more aggressive rehabilitation than would have been possible without the use of the devices, for example, when compared to a primary suture repair alone.

The size and shape of the devices will be dependant upon the size of the defect to be repaired, or of the repair to be augmented. The devices may be approximately the same size as the defect, but may also be larger or smaller. Preferably, the device may be cut, trimmed or tailored by the surgeon to fit the defect in such a way as to not comprise the functionality of the device.

The device may incorporate a barrier to help prevent the formation of adhesions. This barrier may be on just one surface of the device, and can be made from a PHA or other material. For example, the barrier can be incorporated into the device by attaching a PHA film to one surface of the device.

The device should have sufficient structural integrity to allow them to retain sutures or other fixation devices, such as screws or staples, without tearing. The devices should also have sufficient initial strength to prevent a tear within the device. It has been reported that the tensile force applied on the supraspinatus tendon (4 cm in width) of the shoulder can reached 300 N, equivalent to 7.5 N for a strip of tendon 1 mm wide. Ideally, the devices used as interposition devices should have a similar initial failure strength equivalent to at least 7.5 N per mm width of the construct. This value may be determined, for example, by clamping two ends of the device at a 1 cm clamp interval, and then pulling the device in a load call at a rate of 20 cm/min, and calculating the ultimate tensile strength at which the device fails from a force-displacement curve. Augmentation devices may have a lower initial strength as these devices supplement primary repair (e.g., suturing). Preferably, the devices have an initial failure strength of at least 50 N; comprise spores of at least 10 microns, and more preferably over 50 microns in diameter; and are less than 5 mm thick, more preferably less than 3 mm thick, and even more preferably less than 1.5 mm thick.

The devices should be designed to retain strength long enough to allow the body to heal, and permit the patient to return to normal activity. The devices should ultimately resorb, although the time period for the substantial absorption of the devices is less critical than the devices' initial strength retention during the wound healing period.

A preferred composition of the device comprises a non-woven scaffold of poly-4-hydroxybutyrate sandwiched between outer layers of poly-4-hydroxybutyrate knitted multifilament mesh. In one preferred embodiment, the device is prepared from poly-4-hydroxybutyrate multifilament yarn.

If desired, the devices can be manufactured to permit their delivery into the joint through small diameter cannulas while observing through an arthroscope. In these cases, the devices must be flexible, and of a size and shape that permits them to be deployed through a cannula. Prior to delivery, the devices may be compressed, folded, stretched or otherwise placed under tension. If desired, the devices may comprise shape memory materials that cause the devices to open or expand after passing through the cannula. For example, the devices may comprise shape memory rings around their circumference that cause the devices to spring open upon delivery to the implantation site after passage through the cannula. These memory materials may be made from a PHA material, another absorbable material, or from a permanent material such as nitinol.

Fixation Devices

The devices may be fixed at the implantation site by a number of methods including, but not limited to, suturing, stapling, gluing, or the use of suture anchors, tissue tacks, darts, screws, arrows, or any combination thereof. These fixation devices may be preloaded onto the implant or may be added during a surgical procedure.

Additional Device Components

Other materials, including therapeutic, diagnostic, and/or prophylactic agents, cells or whole tissues, may be added to the devices described herein. These materials can be used, for example, to render the devices radio-opaque, simulate tissue in-growth, promote tissue regeneration, prevent adhesion formation, prevent infection, provide additional reinforcement, or modify the porosity of the device.

Exemplary agents include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelmintic agents; antihistamines; antihyperlipidemic agents; antihypertensive agents; anti-infective agents; anti-inflammatory agents; antimigraine agents; antineoplastic agents; antiparkinson drugs; antipruritic agents; antipsychotic agents; antipyretic agents; antispasmodic agents; antitubercular agents; antiulcer agents; antiviral agents; anxiolytic agents; appetite suppressants (anorexic agents); attention deficit disorder and attention deficit hyperactivity disorder drugs; cardiovascular agents including calcium channel blockers, antianginal agents, central nervous system ("CNS") agents, beta-blockers and antiarryhythmic agents; central nervous system stimulants; diuretics; genetic materials; hormonolytics; hypnotics; hypoglycemic agents; immunosuppressie agents; muscle relaxants; narcotic antagonists; nicotine; nutritional agents; parasympatholytics; peptide drugs; psychostimulants; sedatives; sialagogues, steriods; smoking cessation agents; sympathomimetics; tranquilizers; vasodilators; beta-agonist; and tocolytic agents.

For example, an antibiotic may be added to the devices to prevent or treat an infection. The devices may also incorporate autograft, allograft, and/or xenograft materials.

Methods of Manufacture

Manufacture of Filaments

A dry PHA4400 polymer (Tepha, Inc. Cambridge, Mass.), preferably having a moisture content no greater than 50 ppm, is fed into a hopper, extruded through a melt extruder and formed into filaments by a spin head containing filtration media and a multi-hole spinneret. For example, an extruder with a ¾" diameter screw (20:1 l/d) and a 20- to 30-holed spinnerette is used to form a multifilament yarn, and is operated at temperatures below 250° C. The formed filaments are then passed through a hot collar and are quenched in air as they drop from the hot collar.

After quenching, the filament bundle is passed through a finish applicator and then over a series of godet rolls for drawing and relaxing the filaments. The finish applicator applies a spin finish solution to the filaments to assist in subsequent processing. The spin finish solution comprises a lubricating agent and an anti-static agent. Of course, the spin finish may be washed and rinsed or otherwise removed from the yarn after processing is complete.

As the treated filaments are passed over the godet rolls, the filaments are combined in a parallel contiguous arrangement to form a yarn. A tension is applied to the yarn as it passes over the godets to draw the yarn to the desired draw ration. Godet speeds in the range of 2 to 500 meters per minutes are used with preferred draw ration of 5-12. As the yarn leaves the last godet it proceeds to a twister or jet entanglement apparatus.

Formation of Non-Woven Mesh

In jet entanglement, a fluid is forced at elevated pressure into a chamber through which the multi-filament yarn is passed. The fluid is preferably air or some other gas. The turbulence of the gas causes the filament to entangle or intermingle in the area impinged by the jet. The movement of the yarn and the size of the chamber interact to create turbulent pulsations, which entangle the filaments together. Therefore, even with a constant pressure air supply, the yarn can exit the chamber with discrete regularly spaced apart areas of entanglement alternating with non-entangled areas. The yarn retains the entangled portions through subsequent processing steps. As will be appreciated, jet entanglement of the yarn achieves many of the same features of twisting the yarn but at a much higher sped and with a simpler process, thus reducing the costs associated with combining the individual filaments. An example of the properties of a PHA4400 multifilament yarn is given in Table 1.

TABLE 1

Properties of 30-filament P4HB yarn.

| Filament Denier | Total Denier | Tenacity, g/d | Elongation % |
|---|---|---|---|
| 4.4 | 132 | 6.04 | 31% |

Methods of Manufacturing Devices

A preferred composition of the device is assembled by sandwiching the non-woven mesh between knitted multifilament meshes to form a 3-ply construct. Other combinations of the non-woven mesh and knitted multifilament mesh may also be used, including, but not limited to, a 2-ply construct comprising a knitted multifilament mesh with a non-woven mesh. Devices may also be formed from other fiber-based constructs, including monofilament meshes and terrycloth constructs. The multifilament and non-woven layers of the device may be held together, for example, by stitching the layers with fibers of poly-4-hydroxybutyrate, or by other methods such as embroidering or thermal welding. If desired, the device may be further reinforced with mono- or multifilament poly-4-hydroxybutyrate fibers. The edges of the device may also optionally be reinforced ready for implantation to allow, for example, placement of sutures and high resistance to suture pull out. A memory coil may also be incorporated into the edge of the device to assist deployment in vivo if the patch is implanted arthroscopically.

V. Methods of Implantation

The devices may be implanted during surgery, at or in place of the damaged tissue. The TephaFLEX-based device may be placed into the surgical site directly, via an open or a "mini-open" procedure; or it may be placed arthroscopically via a cannula. Ideally, for arthroscopic delivery, the device is easily compressed, rolled or folded or otherwise placed under tension such that smooth and easy passage through the cannula is possible, and the device and be unfolded into its shape for placement, and fixation, into the repair site. After delivery, the devices expand to fit into the desired space.

The present invention may be further understood by reference to the following non-limiting examples.

EXAMPLES

The present invention will be further understood by reference to the following non-limiting examples.

Example 1

Preparation of Knitted Fabric from a Poly-4-Hydroxybutyrate Multifilament Yarn

A multifilament yarn derived according to the procedure described above was knitted into a mesh using a single bar tricot machine (32 and 16 gauge). The width of the mesh was approximately 24 inch. Representative properties of the mesh are given in Table 2.

TABLE 2

Physical Properties of P4HB Knitted Mesh

| Construction | Thickness | Min Burst Strength ASTM D-3786 |
|---|---|---|
| 32 gauge tricot | 0.38 | 259 psi |
| 16 gauge tricot | 0.36 mm | 166 psi |

Example 2

Preparation of a Poly-4-Hydroxybutyrate Non-Woven Mesh

A non-woven mesh was prepared from the multifilament yarn obtained according to the procedure described in Example 1. The yarn was proceed through the following steps:
1) Cone Winding,
2) Crimping and heat setting
3) Chopping to 1"-2" cut length using guillotine cutter
4) Opening for evenly distributed fiber web
5) Carding, multi passes to create fibrous web
6) Needle Punching to interlock the individual fiber
7) Pressing/Heat Setting, 15,000 psi max and 20° C.-70° C.
8) Quilting by either embossing with heated needles or sewing.
9) Scouring and vacuum drying
10) Vacuum Packing Representative properties of the non-woven mesh are given in Table 3.

TABLE 3

Properties of a non-woven mesh made from P4HB multifilament yarn.

| Thickness, ASTM D-1777 | Density | Liquid Porosimetry | Air Permeability | Min Burst Strength ASTM D-3786 |
|---|---|---|---|---|
| 2-5 mm | 300 mg/cc | 600-1700 ml/cm2 | 20-120 Ft3/mm | 210 psi |

Example 3

Preparation of a Poly-4-Hydroxybutyrate Film

A 6 wt/vol % solution of P4HB in chloroform was prepared by dissolving 6 g of P4HB in 100 ml of chloroform. A thin film of P4HB was prepared by casting this solution onto a plate of glass using a 200 mm casting blade (Elcometer Micrometric Film Applicator #357004007). The thickness of the cast solution and the resulting film can be controlled by varying the height of the casting blade or adjusting the concentration of the solution. The chloroform was allowed to evaporate from the cast solution to yield a thin film coating of the P4HB polymer on the glass plate. The film could be removed from the glass intact by wetting the surface with 70% ethanol and peeling the film away. A blade height of approximately 400 μm resulted in a dried film of approximately 16 μm thick.

Example 4

Preparation of a Poly-4-Hydroxybutyrate Interposition or Augmentation Device

A preferred composition of the device is assembled by sandwiching the non-woven mesh of Example 2 between the knitted multifilament meshes of Example 1 to form a 3-ply construct. A particularly preferred device comprising the 3-ply construct described above, made with the 32 gauge tricot construction (shown in Table 2), has the following properties (see also Table 4): thickness of 1.08 mm, pore sizes of approximately 184 μm, and an initial failure strength of 107 N. (The latter was determined on a load cell with a 3-ply construct that is 8 mm wide, using a 1 cm gauge length, and 20 cm/min crosshead speed.) The initial failure strength of the device can be tailored using different constructions. For example, a 2-ply construct can be prepared with an initial failure strength of 78 N using the 32 gauge tricot (shown in Table 2), and a 3-ply construct with the 16 gauge tricot (shown in Table 2) can be prepared with an initial failure strength of 73 N. Thinner devices can also be prepared, for example, from a 2-ply construct of the 32 gauge tricot construction (shown in Table 2) and the non-woven described in Example 2. A 2-ply device made in this manner has a thickness of 0.78 mm (see Table 4). Devices with different porosity can also be prepared. For example, a device comprising the 16-gauge tricot construction shown in Table 2 can be prepared which comprises pores of approximately 242 μm. Initial failure strength may also be tailored according to the need, for example, by incorporating a 32 gauge tricot construction shown in Table 2, instead of the 16 gauge tricot construction also shown in Table 2.

TABLE 4

Examples of properties of Devices

| | 3-Ply Construct (32 needles) | 2-Ply Construct (32 needles) |
|---|---|---|
| Thickness | 1.08 mm | 0.78 mm |
| Ultimate tensile strength | 107 N for 8 mm width | 78 N for 8 mm width |
| Pore size | 184 μm | 184 μm |
| Weight | 9 oz/sq yd (306 g/m$^2$) | 4.5 oz/sq yd (153 g/m$^2$) |

Those skilled in the art will recognize, or be able to ascertain using no more than routine experimentation, many equivalents to the specific embodiments of the invention described herein. Such equivalents are intended to be encompassed by the following

We claim:

1. An interposition or augmentation device for tendon and ligament repair, including rotator cuff repair, comprising poly-4-hydroxybutyrate fibers, wherein the device is porous, has a thickness of less than 5 mm and has an initial breaking load of at least 50 N.

2. The device of claim 1 wherein the device has an initial failure strength of at least 7.5 N per 1.5 millimeter$^2$ of the device.

3. The device of claim 1 wherein the device comprises poly-4-hydroxybutyrate fibers with tenacity greater than 0.1 gram per denier.

4. The device of claim 1 wherein the device retains 50% of its initial strength in vivo for at least 6 weeks.

5. The device of claim 1 wherein the device contains a memory coil.

6. The device of claim 1 in combination with fixation devices, used to fix the implant to either tendon or bone, selected from the group consisting of sutures, tacks, staples and combinations thereof.

7. The device of claim 1 wherein the device contains an active agent selected from the group consisting of therapeutic, diagnostic, and prophylactic agents.

8. The device of claim 7 wherein the active agent is a growth factor.

9. The device of claim 1 wherein the device contains cells either in a native state or cells that have been genetically modified through recombinant techniques.

10. The device of claim 1 wherein the device contains whole tissue selected from the group consisting of autograft, allograft, and xenograft.

11. The device of claim 1 wherein the device comprises one or more layers of a nonwoven mesh, knitted multifilament mesh, monofilament mesh, terrycloth, film, or any combination thereof.

12. The device of claim 1 wherein the device incorporates a barrier to minimize adhesions.

13. An arthroscopic method for the repair of rotator cuff tears comprising placing at a site in need of repair the interposition or augmentation device of claim 1.

14. The method of claim 13 wherein the device is positioned using a canula and arthroscopic guidance.

15. The method of claim 13 wherein the device is positioned surgically.

16. A method for fabricating the interposition or augmentation device of claim 1 comprising forming the device by solvent casting or formation of a non-woven mesh from filaments or yarn woven from fibers of poly-4-hydroxybutyrate.

17. The method of claim 16 wherein the device comprises a multifilament mesh, a non-woven mesh, a monofilament mesh, terrycloth, film, or any combination thereof.

18. The method of claim 17 further comprising areas for sealing together layers of mesh or reinforcing the edges to facilitate suturing.

19. The device of claim 1 wherein the device is an arthroscopic patch.

20. The device of claim 1 wherein device contains pores of at least 10 microns.

21. The device of claim 11, comprising one or more layers of a non woven mesh and a knitted multifilament mesh.

22. The device of claim 21, wherein the non woven mesh is sandwiched between knitted multifilament meshes.

* * * * *